(12) United States Patent
Thomas et al.

(10) Patent No.: US 7,780,712 B2
(45) Date of Patent: Aug. 24, 2010

(54) LAPAROSCOPIC KIDNEY COOLING DEVICE

(76) Inventors: Jonathan Thomas, 8 Monomoy Creek Rd., Nantucket, MA (US) 02554; Sohan Japa, 4851 Lenox Blvd., New Orleans, LA (US) 70131; Mark Bianco, 11340 NW. 23rd St., Pembroke Pines, FL (US) 33026; Thomas Hsu, 698 Gull Ave., Foster City, CA (US) 94404

( * ) Notice: Subject to any disclaimer, the term of this patent is extended or adjusted under 35 U.S.C. 154(b) by 1107 days.

(21) Appl. No.: 11/401,044

(22) Filed: Apr. 10, 2006

(65) Prior Publication Data

US 2008/0008987 A1 Jan. 10, 2008

Related U.S. Application Data

(60) Provisional application No. 60/669,826, filed on Apr. 8, 2005.

(51) Int. Cl.
*A61F 7/00* (2006.01)
(52) U.S. Cl. .................. 607/96; 607/104; 607/113; 604/113
(58) Field of Classification Search .............. 607/96, 607/104, 113, 114; 604/93.01, 113; 128/898
See application file for complete search history.

(56) References Cited

U.S. PATENT DOCUMENTS

| 4,008,754 A | 2/1977 | Kraushaar et al. |
|---|---|---|
| 4,471,629 A | 9/1984 | Toledo-Pereyra |
| 4,473,637 A | 9/1984 | Guibert |
| 5,014,695 A * | 5/1991 | Benak et al. ............ 607/105 |
| 5,542,413 A | 8/1996 | Horn |
| 5,723,282 A | 3/1998 | Fahy et al. |
| 5,821,045 A | 10/1998 | Fahy et al. |
| 5,962,214 A | 10/1999 | Fahy et al. |
| 6,187,529 B1 | 2/2001 | Fahy et al. |
| 6,371,910 B1 * | 4/2002 | Zwart et al. ............ 600/207 |
| 6,685,733 B1 | 2/2004 | Dae et al. |
| 6,692,519 B1 | 2/2004 | Hayes, Jr. |
| 6,736,836 B2 * | 5/2004 | Montgomery ............ 607/104 |
| 2001/0025191 A1* | 9/2001 | Montgomery ............ 607/104 |
| 2006/0025755 A1 | 2/2006 | Landman et al. |

OTHER PUBLICATIONS

Laparoscopic renal parenchymal hypothermia with novel ice-slush deployment mechanism. Ames, C et al., Urology. Jul. 2005;66(1):33-7.
Cryopreservation of organs by vitrification: perspectives and recent advances. Fahy, G et al., Cryobiology. Apr. 2004;48(2):157-78.
Renal hypothermia achieved by retrograde endoscopic cold saline perfusion: technique and initial clinical application. Landman, J et al. Urology. May 2003;61(5):1023-5.
Advances in laparoscopic partial nephrectomy. Touijer K et al. Curr Opin Urol. Jul. 2004;14(4):235-7.

* cited by examiner

*Primary Examiner*—Ahmed M Farah
(74) *Attorney, Agent, or Firm*—Adam W. Bell; Matthew Kaser

(57) ABSTRACT

The present invention encompasses a device for changing the temperature of the kidney during laparoscopic surgery or during organ transportation or transplantation.

14 Claims, 3 Drawing Sheets

LAPAROSCOPIC KIDNEY COOLING DEVICE

This U.S. patent application claims the benefit of U.S. Provisional application No. 60/669,826, filed 8 Apr. 2005 which is hereby incorporated by reference for all purposes.

BACKGROUND

The kidney is a highly vascularized organ. This makes kidney surgery difficult because any incisions into the organ tend to cause large amounts of bleeding. During laparoscopic surgery blood flow to the kidney is often interrupted by clamping off the renal artery. During this time of blood flow deprivation, the kidney may easily become damaged by ischemia. Very significant damage can occur after thirty minutes of blood flow deprivation. Because of ischemic damage, surgery tends to be done as quickly as possible. To reduce the rate of ischemic damage, the kidney may be cooled before operating. Lowering the temperature of the organ reduces the rate at which ischemic damage is caused because it slows the local metabolic rate of the organ and reduces catabolic enzymic activity.

A number of disclosures exist that describe the cooling of organs prior to or during transportation for transplantation. Transfusion of cold saline into the kidney via the uterer or renal artery has been described, but neither technique appears to produce sufficient cooling of the cortex of the kidney to prevent ischemic damage. In order to avoid ischemic damage, the kidney parenchyma should preferably reach about 15° C., but these two current methods produce parenchymal temperatures of only about 21-24° C., insufficient to avoid damage. Additionally, injecting water through the renal artery may lead to renal artery injury and thrombosis. Another solution employs a tubular "Endocatch II" bag (United States Surgical, Norwalk, Conn.) placed around the kidney and through which coolant (an ice slush) is pumped. Using this technique, Touijer et al have been able to produce parenchymal temperatures of between 5° C. and 19° C. within 10 minutes. But in order to perform surgery, the bag must be removed. The kidney quickly warms, allowing ischemia to occur.

A number of patent disclosures describe relevant methods and devices for cooling organs. Many of these disclosures, however, relate to cooling organs during transportation after the organs have been removed from the body for transplantation.

U.S. Pat. No. 4,008,754 describes a method of organ preservation comprising rinsing the organ with an inert gas until it is free of water and blood. The vascular system is thus filled with the inert gas or gas and the organ is cooled in an inert gas atmosphere to a temperature below minus 100° C.

U.S. Pat. No. 4,471,629 describes a method of freezing and transplanting a kidney. This method uses the successive step of infusing pressurized chilled helium into the renal artery while progressively and rapidly cooling the kidney located on a support of a container that is not immersed but surrounded by a body of liquid nitrogen. A further step includes the thawing of the frozen kidney by application of infrared radiation to the kidney within a confined area while continuously rotating the kidney for uniform thawing, much like a traditional rotisserie.

U.S. Pat. No. 4,473,637 describes a system for processing an organ such as a kidney so as to render it suitable for storage, shipment and eventual transplantation. After its removal from a donor, the organ is cradled in a net suspended within a basin. A preservative fluid initially at normal blood temperatures progressively cooled to avoid thermal shock, the fluid being pumped through the organ to flush out its natural fluids. The pumping action is such as to simulate that of the heart and its associated circulatory system. The exterior of the organ is chilled by simultaneously introducing the preservative fluid into the basin. After this chilling procedure is completed, the cradle carrying the cooled organ is transferred to a basin disposed in a thermally-insulated shipping box which is then filled with chilled preservative fluid and maintained at a desired low temperature level by an associated refrigeration unit. Just prior to transplantation, the cradle carrying the organ is removed from the box and the organ is again flushed, using the same procedure as in chilling but in reverse, the preservative fluid being raised to a temperature level close to normal blood temperature. Upon completion of this procedure, the organ is in condition for transplantation.

U.S. Pat. No. 6,692,519 describes methods for preventing hypoxic damage to a potentially transplantable organ prior to explanation of that organ or tissue from the body of a donor. The methods comprise placing a heat exchange apparatus in the vasculature of the donor or recipient and using that heat exchange apparatus to cool at least a portion of the body of the donor or recipient to a temperature below 36° C.

U.S. Pat. No. 5,723,282 describes a Method for preparing organs for cryopreservation through the introduction of a chilled liquid into the organ to reduce the temperature of the organ to as low as minus 5° C.

Prior to the present disclosure, no method or device has existed to cool the kidney in situ, during laparoscopic surgery, providing adequate cooling and without damaging the kidney.

BRIEF DESCRIPTION OF THE INVENTION

The present invention encompasses a device for changing the temperature of the kidney during laparoscopic surgery or during kidney removal or implantation (transplantation). The invention is essentially a bag shaped and sized for receiving a kidney, the bag having a plurality of tubes or channels implanted within its walls, through which cold fluid is pumped. The bag includes one or more windows that may be opened in the bag at any of a number of locations, providing access to the kidney at any desired site while allowing uninterrupted cooling of the kidney, thereby reducing ischemic damage during surgery when blood flow is interrupted.

The present invention encompasses a number of particular embodiments, as follow.

In one embodiment, the invention encompasses a device for heating or cooling an organ, the device comprising an enclosure sized and shaped to receive an organ. The enclosure is defined broadly to include any structure that may, in use, substantially enclose or surround a desired organ. The enclosure may generally have at least one fluid reservoir within it. The fluid reservoir may simply be defined by the space between the walls of the enclosure, such as provided by a bi-layered bag, or may be more complex, for example it may include a plurality of bladders arranged an any particular geometry on or in the enclosure. The purpose of the fluid reservoir is to retain a fluid which is provided to cool or heat the enclosed organ. The enclosure may also or alternatively have one or more fluid channels disposed within it for the same purpose. Fluid channels may be provided to allow circulation of a fluid through the channels and within the structure of the enclosure. In various preferred embodiments, at least a portion of the enclosure (a window) is openable so as to expose an area underneath it. The openable portion may be re-sealable or non re-sealable. A re-sealable portion may be provided by use of a plastic channel-and-grove zip (Ziploc®) structure or hook-and-eye fastener. A non re-sealable portion may be provided by a perforated region such as may be easily created by a standard plastic-molding process.

The enclosure is generally sized and shaped to substantially (say about 50%, 75%, 85%, 95% or 100%) surround the organ received therein.

The enclosure may comprise a first opening adapted in size and shape and position to receive the organ, i.e., it is through this opening that the organ will be inserted or by which the enclosure will be placed over and around the organ. The enclosure may also include a separate openable window adapted to allow access to the organ when the device is in use. In certain embodiments, the first opening extends substantially along one entire side of the enclosure.

The enclosure may be a bag-shaped structure having a first opening adapted to receive the organ, and at lease one separate openable window. In an alternative embodiment, the enclosure can be a sheet-shaped structure sized and shaped to be folded around an organ so as to substantially enclose the organ, and when enclosing the organ, to provide at least one openable window adapted to allow access to the organ.

In a number of preferred embodiments, the device is adapted to be used with an internal organ such as a kidney, liver, lung, bladder, uterus, pancreas, gall-bladder, blood vessel, eye, spinal tissue or heart. The device may adapted for any organ, either internal or external.

In a preferred embodiment the device has a fluid reservoir or fluid channel in fluid communication with one or more fluid-conducting tubes through which a cooling fluid is flowed.

In a preferred embodiment the device comprises a bi-layered structure with a plurality of fluid channels disposed within it. The plurality of fluid channels may be configured as interlocking "fingers" (interdigitated).

The interdigitated finger design lends itself particularly well to a design in which a serpentine arrangement of channels is threaded within the structure of the device allowing a single finger to be separated to expose an area underneath it without breaking the continuity of the fluid flow through the channels. However, it should be understood that the term "finger" is not meant to limit the shape of the part, but is used generally to describe any part that performs the function described herein. The fingers used herein may be elongated, generally rectangular, round, ovoid, curved, L-shaped or of absolutely any desired shape.

In some embodiments there is only one finger, in others there may be a plurality of fingers positioned within the device.

The fingers may be juxtaposed, one next to the other, or alternatively, the fingers may be individually placed or spaced on the device.

The interlocking fingers can be patterned in an approximately zigzag pattern, each alternately interdigitating with the next. The fingers may be detachable or non-detachable from the body of the device, i.e., each finger can be defined by alternating sealed and/or detachable (re-sealable or non resealable) regions, wherein an individual finger may be peeled back and separated from the body of the enclosure to expose an area underneath it. In certain embodiments, the detachable regions are perforated regions to allow non-re-sealable detachment.

In a one embodiment the device encompasses a bi-layered enclosure with an outer layer and an inner layer wherein said outer layer conducts heat less efficiently than said inner layer, and wherein said inner layer, when in use, is generally in contact with an organ received within the bi-layered enclosure.

The invention also encompasses a method for cooling an organ, the method comprising: providing the device as described herein and positioning an organ within the device such that the device is generally in contact with an organ, and providing a cooling fluid within at least one fluid reservoir or fluid channel of the device.

DETAILED DESCRIPTION OF THE INVENTION

Figure 1:
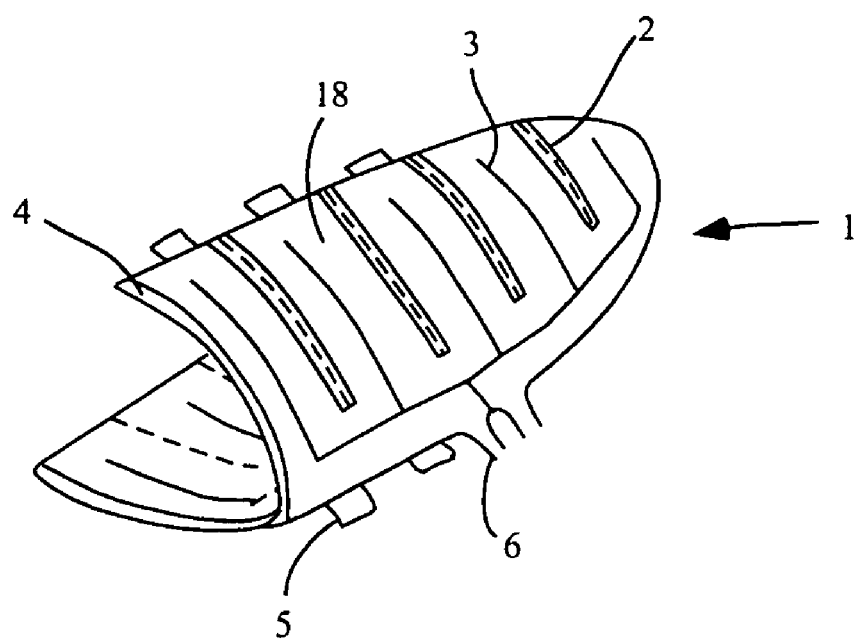
FIG. 1 is a perspective view of the device, showing the body of the device (1) in a partially open position. The body of the device comprises a bi-layered bag with fluid channels (18) within it, configured in an approximately zigzag pattern. The interlocking "finger" structure is defined by sealed lines (3) and perforated lines (2). When the perforated lines are peeled back from the body of the device, an exposed access area is revealed underneath allowing access to the kidney within the bag. Tabs (5) are provided for securing the fingers of the bag in the closed or open position. Fluid channels are shown (6) through which cooling or heating liquid or gas may be pumped. Also visible is the edge portion of the bag containing a guide (4) adapted to receive the pre-stressed C-shaped member (17).
Figure 2:
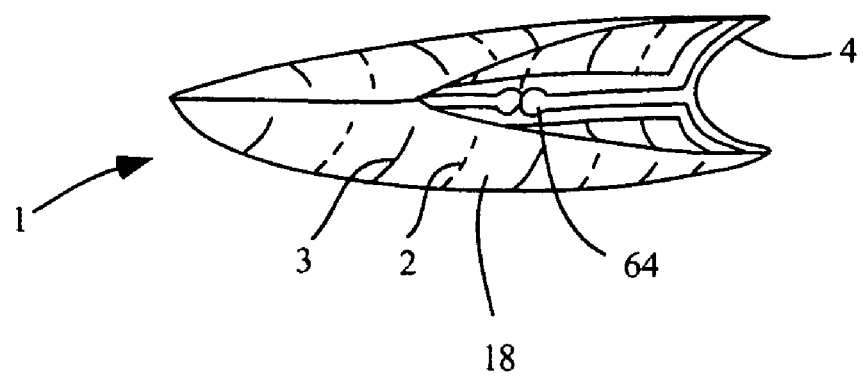
FIG. 2 is another perspective view of the device showing the interior with fluid channels (6) visible from the inside of the device.
Figure 3:
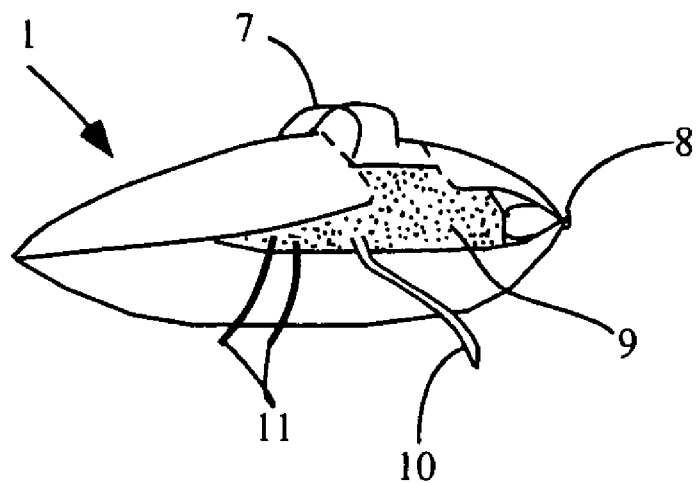
FIG. 3 is a perspective view of the device in use, having a kidney (9) cradled within it, with renal blood vessels (11) and the ureter (10) shown extending from the device. The end of the device is secured with a surgical clip (8). A finger portion (7) is shown peeled back to expose a portion of the kidney (9).
Figure 4:
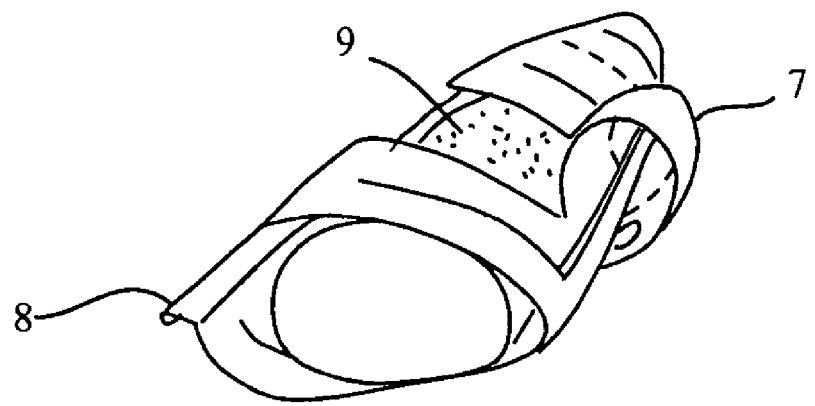
FIG. 4 is another perspective view of the device retaining a kidney with finger portion peeled back to expose a portion of the kidney.
Figure 5:
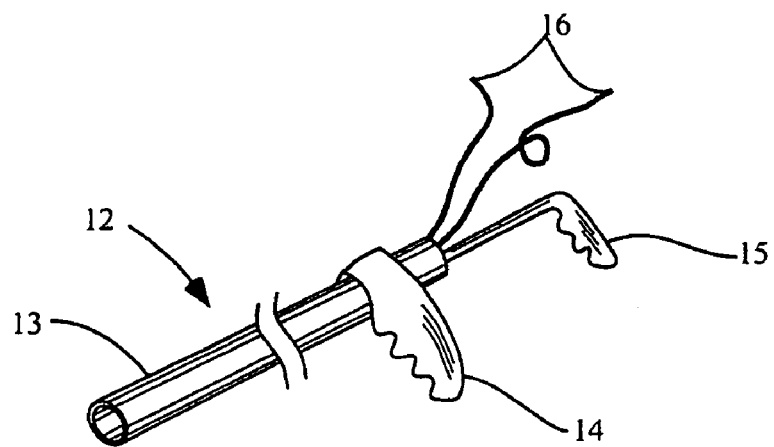
FIG. 5 is a perspective view of a laparoscope (12) used to deploy the device of the invention. The shaft of the laparoscope is a cylinder (13) that houses the invention with the intake and outlet tubes (16) extending behind it. A handle (14) and a manipulator (15) are used to position the laparoscope and deploy the device. Once the bag is fully deployed from within the cylinder, the surgeon can guide the bag onto the kidney. The deployment tube is then retracted from the abdomen.
Figure 6:
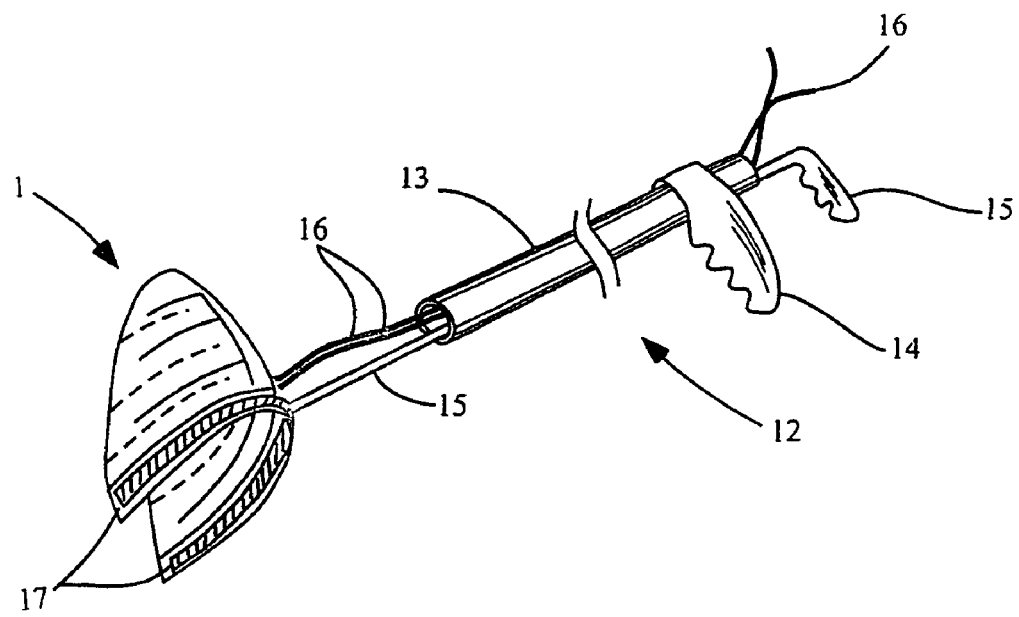
FIG. 6 shows a perspective view of the device (1) of the invention being deployed via a laparoscope (12). The two fluid tubes (16) which are connected to the fluid channels are shown (6) are shown at either end of the laparoscope. Also shown are the manipulator (15), the laparoscope handle (14), and laparoscope cylinder (13). Additionally, this view shows the pre-stressed C-shaped member (17) that, in use, maintains the oval opening and simplifies positioning of the device. The shaft of the manipulator (15) runs through the laparoscope cylinder (13) and is attached to the pre-stressed C-shaped member (17).

The present invention encompasses a device for cooling the kidney during laparoscopic surgery. The device may also be used during organ transplantation to cool the organ of the donor before removal of the kidney. The device could also be used to keep the kidney cool while transporting the organ, and during implantation of the organ into the recipient. Further, the device could be used to help warm the organ in the abdomen of the receiving patient by pumping warm fluid through the bag.

In its simplest embodiment, the invention is essentially a bag (1) shaped and sized for receiving a kidney (9), the bag having a plurality of tubes or channels (18) implanted within its walls, through which a cold fluid is pumped via fluid channels (6). A window may be opened in the bag by peeling back a finger (7) at any of a number of locations. This provides access to the kidney (9) at any desired site, while simultaneously allowing uninterrupted cooling of the kidney, thereby reducing the rate of ischemic damage. The bag and the channels within it may have any number of structural embodiments so long as the basic functions are fulfilled.

In certain embodiments, the device comprises a bag (1), shaped and sized to receive a kidney (9), wherein the wall of the bag is formed from a plurality of "fingers" (7) that are approximately parallel strips that may be temporarily pealed back to reveal a portion of the kidney surface underneath. These fingers are separated by alternating sealed lines (3) and detachable perforated lines (2) so as to allow for easy separation during surgery. The wall of the bag contains a network of integrated tubes or channels (18) through which a fluid, such as a cooling fluid, may be conducted. The interior surface of the bag is designed so that it is generally in contact with the surface of the kidney retained within it. Such contact allows heat to be conducted from the kidney tissue to the cooling fluid in accordance with the second law of thermodynamics. One or more fluid entry and exit ports (6) are provided so that fluid may be pumped into and out of the network of channels (18). The fluid entry points are designed to be connected to conduits (16) that conduct fluid to and from an external source. A slit in the side of the bag is provided so that the ureter (10) and renal blood vessels (11) may extend unimpeded from the bag during the entire surgical procedure. The surfaces of the bag may be made of dissimilar materials so as to improve the heat transfer behavior of the device. For example, the internal surface may be highly conductive, while the external surface may be insulating so as to protect the surrounding abdominal organs from undesirable cooling.

In a preferred embodiment, a fluid, e.g., a saline solution at a temperature slightly below zero degrees Celsius, is pumped through the network of tubes or channels (18) lining the bag interior. Sterilized ice water slurry may also be used as a cooling fluid.

The fluid is cooled using any suitable cooling device such as a traditional commercially-available refrigeration unit. The fluid may be pumped through the channels using any suitable fluid pumping system, for example, a peristaltic pump. The pump is connected to the intake tube and has a flow control valve to adjust flow rate.

The rate and degree of cooling will depend on the temperature of the coolant, the temperature of the kidney, the rate of flow of the fluid through the channels, the surface area of contact between the kidney tissue and the interior surface of the bag, and the heat conductivity of the bag-tissue interface.

In various embodiments, the degree of contact between the interior surface of the bag and the kidney tissue is enhanced by the inflation of the bag while in contact with the kidney. Inflation is caused by the coolant fluid itself, which fills the channels, inflating the bag and pressing its inner walls snuggly against the kidney.

In a preferred embodiment, the channels are separated by a perforated line portions (2) configured in a zigzag pattern so as to allow liquid to flow through the interconnected channels (18) and throughout the entire bag. The ultimate structure resembles interlocked figures of two opposing hands. The perforated lines on either side of one "finger" can be torn to separate and free the finger to allow access to the kidney tissue underneath.

A preferred embodiment has between two and six, preferably four of these perforated sections on each side of the bag. This allows the surgeon to expose a section of the kidney by tearing a specific perforation and peeling back the appropriate water channel. The rest of the kidney will continue to be cooled for the duration of the operation.

In one embodiment, the bag is created from two layers of polystyrene, polypropylene, or polyethylene plastic that are joined using a heated bag sealer. The intake and exit tubes (16) are then attached to the bag in a fluid-tight fashion.

In certain embodiments, the bag may be deployed using a standard 12 mm diameter laparoscopic device (12). The shaft (13) of the device houses the bag (rolled up) with the intake and outlet tubes extending behind it. The device is placed into the patient through a trocar. For deployment, a hand actuated trigger activates a piston that pushes the bag outward from within the device's main cylinder. Once the bag is fully deployed from within the cylinder, the surgeon can guide the bag onto the kidney. The deployment tube is retracted from the abdomen after the bag has been placed in the proper position. One advantageous feature of the current invention is to be deployed through a standard laparoscopic trocar. The invention is easy to use with existing hardware, which reduces the cost accordingly.

In various embodiments, the bag device shaped in the form or a hood or bonnet. The hooded bag simplifies placement of the bag on the kidney; with one end of the bag fully closed, the doctor can control the position of the bag from the opposite end. The hood is much like a hood of a sweatshirt allowing the bag to be pulled over the kidney until the hood contacts the organ. The bag may include a fastening mechanism (hook and eye, string, tape, or surgical clips) to secure the non-hooded end of the bag. The bag is unfurled by pulling it over the kidney something like putting a sock on a foot.

In other embodiments, to further aid in bag placement, the leading edge of the bag is provided with a pre-stressed C-shaped member (17) terminally fixed to a manipulator shaft (15) that extends through the deployment tube (13). The C-shaped member is disposed within a guide channel (4) at the edge of the bag. The manipulator shaft and the C-shaped member are rigidly attached together to form a laterally stiff unit whereby the C-shaped member may be manipulated via the manipulator to position the device over the kidney. In use, the bag portion of the device is guided over and around the kidney using the C-shaped member. The C-shaped member maintains the oval opening and simplifies the encapsulation process. After encapsulation, the C-shaped member may be withdrawn out of the guide channel by pulling on the manipulator. Alternatively the manipulator and the C-shaped member may be detached, leaving the C-shaped member in the guide channel. If repositioning of the device is required later, the manipulator and the C-shaped member may be reattached.

ALTERNATIVE EMBODIMENTS

Although the embodiment mainly described herein is that of a cooling device used to cool the kidney during an operation, the device may also be used during organ transplantation to cool the organ of the donor before removal of the kidney. The device could also be used to keep the kidney cool while transporting the organ, and during implantation of the organ into the recipient. Further, the device could be used to help warm the organ in the abdomen of the receiving patient by pumping warm fluid through the bag.

The present device may also be employed for a number of other potential applications. For example, the device may be used to cool other organs during surgery, particularly if it is necessary to restrict or halt blood flow to the organ during the operation. In such cases, the device would be sized and shaped to receive the organ in question, for example the heart, liver, bladder, uterus, etc. In other embodiments the device may be used to cool an external organ or even a limb during an operation, for example, the hand, arm, foot, testicles etc. The design of the bag will be varied to fit the body part in question.

The main embodiment described herein employs a roughly rectangular finger system, but the removable portions of the bag could take various shapes, for example round, oval etc.

The embodiments disclosed in this document are illustrative and exemplary and are not meant to limit the invention. Other embodiments can be utilized and structural changes can be made without departing from the scope of the claims of the present invention. As used herein and in the appended claims, the singular forms "a", "an", and "the" include plural reference unless the context clearly dictates otherwise. Thus, for example, a reference to "a part" includes a plurality of such parts, and so forth.

The invention claimed is:

1. A device for heating or cooling an organ, the device comprising a enclosure sized and shaped to receive an organ, said enclosure having at least one fluid reservoir or fluid channel disposed within it, and wherein at least a portion of the enclosure is openable so as to expose an area underneath it, and wherein the enclosure comprises a bi-layered structure, and wherein said bi-layered structure has a plurality of fluid channels disposed within it, and wherein the plurality of fluid channels are configured as interlocking fingers and wherein an individual interlocking finger is detachable and may be peeled back and separated from the enclosure to expose an area underneath it.

2. The device of claim 1 wherein, in use, the enclosure is sized and shaped to substantially surround the organ received therein.

3. The device of claim 2 wherein, in use, the enclosure comprises a first opening adapted to receive the organ, and a separate openable window adapted to allow access to the organ.

4. The device of claim 3 wherein the first opening extends substantially along one entire side of the enclosure.

5. The device of claim 1 wherein the organ is an internal organ.

6. The device of claim 1 sized and shaped to receive a kidney.

7. The device of claim 1 wherein said fluid reservoir or fluid channel is in fluid communication with one or more fluid-conducting tubes.

8. The device of claim 1 wherein the interlocking fingers are patterned in an approximately zigzag pattern.

9. The device of claim 1 wherein said detachable finger is bounded by a perforated region.

10. The device of claim 1 wherein the bi-layered enclosure has an outer layer and an inner layer and wherein said outer layer conducts heat less efficiently than said inner layer, and wherein said inner layer, when in use, is generally in contact with an organ received within the bi-layered enclosure.

11. A method for cooling an organ, the method comprising:
providing a device for heating or cooling an organ, the device comprising a enclosure sized and shaped to receive an organ, said enclosure having at least one fluid reservoir or fluid channel disposed within it, and wherein at least a portion of the enclosure is openable so as to expose an area underneath it, and wherein the enclosure comprises a bi-layered structure, and wherein said bi-layered structure has a plurality of fluid channels disposed within it, and wherein the plurality of fluid channels are configured as interlocking fingers and wherein an individual interlocking finger is detachable and may be peeled back and separated from the enclosure to expose an area underneath it,
providing an organ,
positioning the organ within the device such that the device is substantially in contact with an organ, and
providing a cooling fluid within at least one fluid reservoir or fluid channel of the device so as to cool the organ.

12. The method of claim 11 wherein said fluid reservoir or fluid channel is in fluid communication with one or more fluid-conducting tubes and wherein the method further comprises pumping a cooling fluid through the fluid reservoir or fluid channel of the device.

13. The method of claim 11 wherein the organ is an internal organ.

14. The method of claim 13 wherein the organ is a kidney.

* * * * *